United States Patent [19]
Pavlin et al.

[11] Patent Number: 5,998,570
[45] Date of Patent: Dec. 7, 1999

[54] ESTER-TERMINATED POLYAMIDES OF POLYMERIZED FATTY ACIDS USEFUL IN FORMULATING TRANSPARENT GELS IN LOW POLARITY LIQUIDS

[75] Inventors: Mark S. Pavlin, Lawrenceville; Richard C. MacQueen, Phillipsburg, both of N.J.

[73] Assignee: Union Camp Corporation, Wayne, N.J.

[21] Appl. No.: 09/074,070

[22] Filed: May 6, 1998

Related U.S. Application Data

[62] Division of application No. 08/734,523, Oct. 18, 1996, Pat. No. 5,783,657.

[51] Int. Cl.$^6$ .......................... C08G 63/00; C08L 67/00; C08L 77/00
[52] U.S. Cl. .......................... 528/310; 528/272; 528/288; 528/292; 528/302; 528/324; 528/326; 528/339; 44/275; 252/522 A; 524/219; 524/606; 525/411; 525/420.5; 525/425; 525/434; 431/288
[58] Field of Search .......................... 528/272, 288, 528/292, 302, 310, 324, 326, 339; 44/275; 252/522 A; 524/219.606; 525/411, 420.5, 425, 434; 431/288

[56] References Cited

U.S. PATENT DOCUMENTS

| | | | |
|---|---|---|---|
| 2,379,413 | 7/1945 | Bradley | 260/404.5 |
| 2,450,940 | 10/1948 | Cowan et al. | 260/404.5 |
| 2,662,068 | 12/1953 | Floyd | 260/33.6 |
| 3,141,787 | 7/1964 | Goetze et al. | 106/252 |
| 3,148,125 | 9/1964 | Strianse et al. | 167/85 |
| 3,156,272 | 11/1964 | Carlick et al. | 106/27 |
| 3,341,465 | 9/1967 | Kaufman et al. | 252/316 |
| 3,615,289 | 10/1971 | Felton | 44/7.5 |
| 3,645,705 | 2/1972 | Miller et al. | 44/7.5 |
| 4,051,159 | 9/1977 | Tsoucalas et al. | 260/404.5 |
| 4,062,819 | 12/1977 | Mains et al. | 260/18 |
| 4,115,370 | 9/1978 | Corrado | 260/22 CQ |
| 4,128,436 | 12/1978 | O'Hara et al. | 106/243 |
| 4,150,002 | 4/1979 | Drawert et al. | 260/18 |
| 4,275,054 | 6/1981 | Sebag et al. | 424/65 |
| 4,337,298 | 6/1982 | Karim et al. | 428/461 |
| 4,341,671 | 7/1982 | Bolze et al. | 528/324 |
| 4,346,024 | 8/1982 | Coquard et al. | 524/219 |
| 4,376,194 | 3/1983 | Tanaka et al. | 528/288 |
| 4,438,240 | 3/1984 | Tanaka et al. | 525/420 |
| 4,552,693 | 11/1985 | Hussain et al. | 252/522 A |
| 4,571,267 | 2/1986 | Drawert et al. | 106/27 |
| 4,663,428 | 5/1987 | Okitu et al. | 528/324 |
| 4,769,285 | 9/1988 | Rasmussen | 428/355 |
| 4,937,069 | 6/1990 | Shin | 424/66 |
| 5,069,897 | 12/1991 | Orr | 424/66 |
| 5,102,656 | 4/1992 | Kasat | 424/66 |
| 5,342,894 | 8/1994 | Robeson et al. | 525/183 |
| 5,372,852 | 12/1994 | Titterington et al. | 427/288 |
| 5,500,209 | 3/1996 | Ross et al. | 424/66 |
| 5,538,718 | 7/1996 | Aul et al. | 424/64 |
| 5,645,632 | 7/1997 | Pavlin | 106/31.29 |

OTHER PUBLICATIONS

Yasuda et al., "Novel Low–molecular–weight Organic Gels: N,N',N"—Tristearyltrimesamide/Organic Solvent System," *Chemistry Letters*, pp. 575–576, 1996. The month in the date of publication is not available.

*Primary Examiner*—P. Hampton-Hightower
*Attorney, Agent, or Firm*—Seed and Berry LLP

[57] ABSTRACT

A low molecular weight, ester-terminated polyamide may be blended with a liquid hydrocarbon to form a transparent composition having gel consistency. The ester-terminated polyamide is prepared by reacting "x" equivalents of dicarboxylic acid wherein at least 50% of those equivalents are from polymerized fatty acid, "y" equivalents of diamine such as ethylene diamine, and "z" equivalents of monoalcohol having at least 4 carbon atoms. The stoichiometry of the reaction mixture is such that $0.9 \leq \{x/(y+z)\} \leq 1.1$ and $0.1 \leq \{z/(y+z)\} \leq 0.7$. The reactants are heated until they reach reaction equilibrium. The gel contains about 5–50% ester-terminated polyamide with the remainder preferably being pure hydrocarbon. The gels are useful in formulating personal care products and other articles wherein some degree of gel-like or self-supporting consistency is desired.

24 Claims, 1 Drawing Sheet

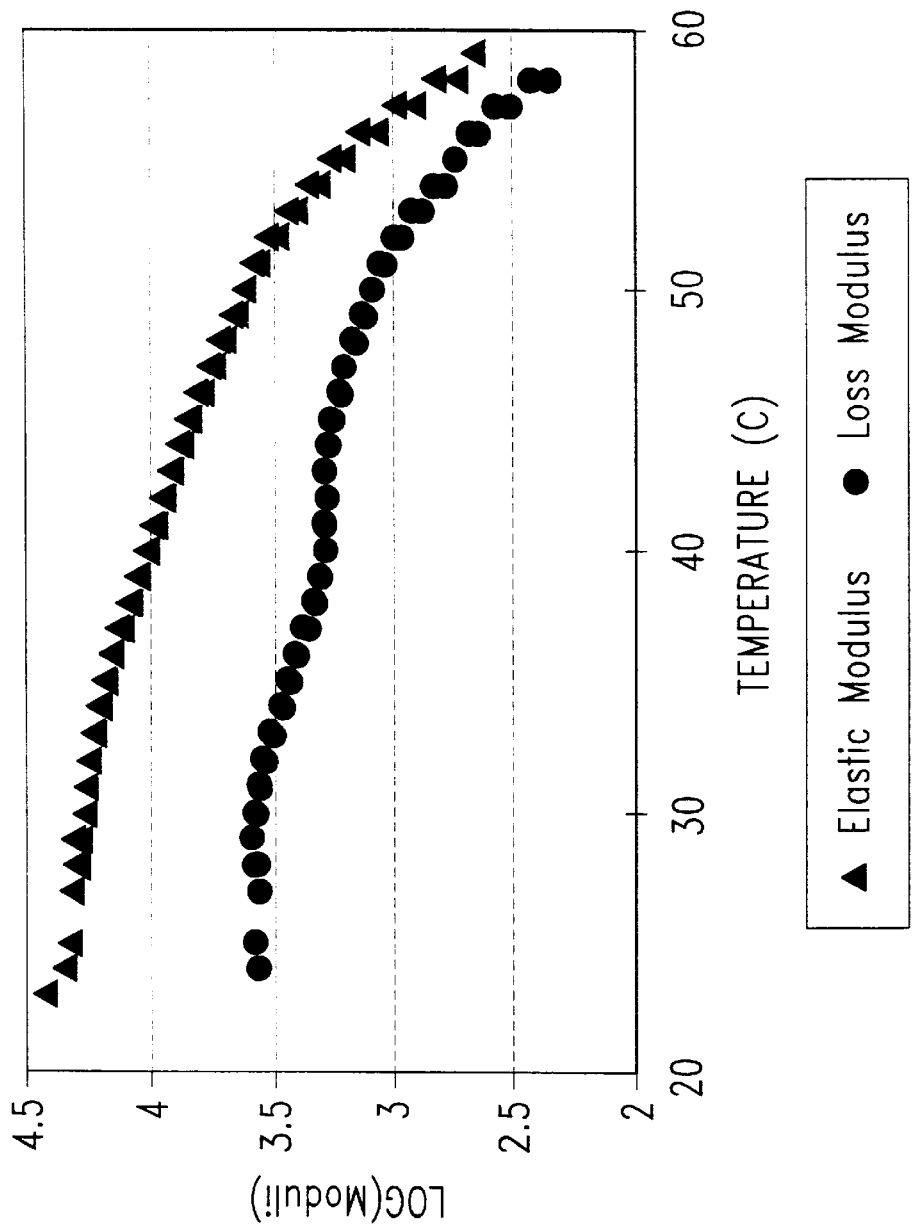

ESTER-TERMINATED POLYAMIDES OF POLYMERIZED FATTY ACIDS USEFUL IN FORMULATING TRANSPARENT GELS IN LOW POLARITY LIQUIDS

CROSS-REFERENCE TO RELATED APPLICATION

This application is a Divisional of U.S. patent application Ser. No. 08/734,523, filed Oct. 18, 1996, now U.S. Pat. No. 5,783,657, issued Jul. 21, 1998.

TECHNICAL FIELD OF THE INVENTION

The invention relates to gelling agents and in particular to gellants for low polarity liquids such as hydrocarbons.

BACKGROUND OF THE INVENTION

Personal care products generally contain one or more active ingredients within a carrier formulation. While the active ingredient(s) determine the ultimate performance properties of the product the carrier formulation is equally critical to the commercial success of the product. The rheology of the carrier (also referred to as the "base") largely determines the flow properties of the product, and the flow properties largely determine the manner in which the consumer will apply or use the product.

For example aluminum chlorohydrate and aluminum-zirconium tetrachlorohydrex-Gly are metal salts that are commonly used as active ingredients in deodorant and antiperspirant products. Consumers have shown a preference for applying deodorant from a stick form. Thus, the carrier in a stick-form deodorant must be a relatively hard substance and waxy fatty alcohol such as stearyl alcohol has been used as the carrier in these products. As another example, the active ingredient in a lipstick is the colorant. A lipstick should not be as hard as a stick deodorant, but of course must maintain its shape when undisturbed at room temperature. A blend of wax and oil is known to provide a consistency that is well-suited as a carrier for a lipstick. As a final example, shampoo desirably has a viscosity greater than water, and when the active ingredient(s) in a shampoo does not have a sufficiently high viscosity, a somewhat viscous carrier material is desirably included in the shampoo formulation.

From the above examples, it is seen that formulators of personal care products depend upon the availability of materials having various rheological properties, in order to formulate a successful personal care product. Materials which have a gel-like character, in that they maintain their shape when undisturbed but flow upon being rubbed, are often desired for personal care products.

Transparent (i.e., clear) carriers are needed by formulators who develop a personal care product wherein colorant is an active ingredient, because a transparent carrier (as opposed to an opaque carrier) will minimally, if at all, interfere with the appearance of the colorant. However, in recent years consumers have demonstrated an increasing preference for transparent personal care products such as deodorants and shampoos. There is thus an increasing demand for transparent materials which can provide the rheological properties needed for various personal care products, and particularly which can impart gel-like character to a formulation.

Polyamide resin prepared from polymerized fatty acid and diamine is reported to function as a gellant in formulations developed for personal care products. For example. U.S. Pat. No. 3,148,125 is directed to a clear lipstick composition formed from polyamide resin compounded with a lower aliphatic alcohol and a so-called "polyamide solvent." Likewise, U.S. Pat. No. 5,500,209 is directed to forming a gel or stick deodorant, where the composition contains polyamide gelling agent and a solvent system including monohydric or polyhydric alcohols. Thus, the prior art recognizes to blend certain polyamides with alcohols, to thereby form a gel.

Certain modified polyamide resins, e.g., polyamides which are only partly amidated but contain esterified carboxyl groups, have been reported to impart high gel strength and pronounced thixotropic properties to coating compositions that contain alkyd resins or drying oils. See U.S. Pat. No. 3,141,767 to Goetze et al. However, the modified polyamide resins of Goetze et al. are not disclosed as being useful gellants in personal care products, nor useful gellants when pure hydrocarbon is used as the vehicle.

Pure hydrocarbon is desirably included in a personal care formulation because it is transparent and relatively inexpensive. Pure hydrocarbons are also available in a wide variety of viscosities and grades. However, pure hydrocarbon often does not have the rheological properties that are desired in a carrier, e.g., it does not naturally exhibit gel-like character. When hydrocarbon is present in a personal care formulation alcohol is also typically present when a gel-like consistency is desired for the product. There is a need in the art for materials which can be combined with pure hydrocarbon to afford a transparent material which has gel-like character. The present invention provides this and related advantages as described herein.

SUMMARY OF THE INVENTION

The present invention is directed to a resin composition comprising ester-terminated polyamide (ETPA) of formula (1):

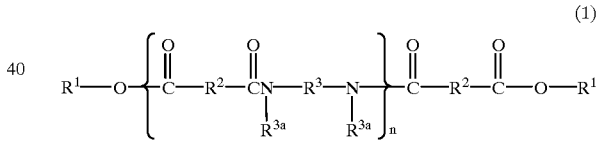

wherein n designates a number of repeating units such that ester groups constitute from 10% to 50% of the total of the ester and amide groups; $R^1$ at each occurrence is independently selected from an alkyl or alkenyl group containing at least 4 carbon atoms; $R^2$ at each occurrence is independently selected from a $C_{4\text{-}42}$ hydrocarbon group with the proviso that at least 50% of the $R^2$ groups have 30–42 carbon atoms; $R^3$ at each occurrence is independently selected from an organic group containing at least two carbon atoms in addition to hydrogen atoms, and optionally containing one or more oxygen and nitrogen atoms: and $R^{3a}$ at each occurrence is independently selected from hydrogen $C_{1\text{-}10}$alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen. Preferably, the resin composition further comprises diester having formula (1) wherein n=0. such that the ratio of ester groups to the sum of ester and amide groups in the total of the ester-terminated polyamide and diester is from 0.1 to 0.7. Preferably, the resin composition is at reaction equilibrium.

Another aspect of the invention is a method for preparing a resin composition comprising ester-terminated polyamide.

The method comprises reacting x equivalents of carboxylic acid from diacid or a reactive equivalent thereof, y equivalents of amine from diamine and z equivalents of hydroxyl from monoalcohol or a reactive equivalent thereof. At least about 50% of the carboxylic acid equivalents are from polymerized fatty acid, and monoalcohol is substantially the only monofunctional reactant used to form the resin. The monoalcohol has at least four carbon atoms, $0.9 \leq \{x/(y+z)\} \leq 1.1$, and $0.1 \leq \{z/(y+z)\} \leq 0.7$. The invention also includes the resin composition prepared by the inventive method.

A further aspect of the invention is a composition comprising a low polarity liquid and at least one resin composition which is described above, i.e., a resin composition comprising ester-terminated polyamide of formula (1):

(1)

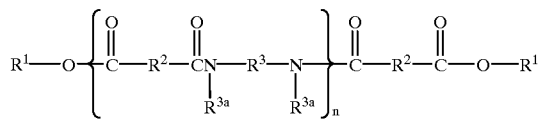

wherein n, $R^1$, $R^2$ and $R^3$ are set forth above, or the resin composition prepared by the method of reacting x equivalents of carboxylic acid from diacid or a reactive equivalent thereof, y equivalents of amine from diamine and z equivalents of hydroxyl from monoalcohol or a reactive equivalent thereof as described above.

Another aspect of the invention is a method for preparing a transparent or translucent gel. The method comprises combining a low polarity liquid with a resin composition, where the resin composition contains ETPA as described above, or has been prepared by the methods described above.

A further aspect of the invention is a candle comprising a wick and a resin composition where the resin composition contains ETPA as described above, or has been prepared by the methods described above.

Another aspect of the invention is a cosmetic which comprises the resin composition containing ETPA as described above or which has been prepared by the methods described above.

The invention also includes articles of manufacture comprising ester-terminated polyamide as described above. Such articles include antiperspirants and cosmetics, as well as other personal care products (e.g., deodorant, eye make-up, lipstick, foundation make-up, baby oil, make-up removers bath oil, skin moisturizers, sun care products, lip balm, waterless hand cleaner, medicated ointments, ethnic hair care products perfume, cologne, costume make-up and suppositories), candles and other household products (e.g., automobile wax, automobile polish, furniture polish, metal cleaners, metal polish, household cleaners, paint strippers and insecticide carriers) and industrial products (e.g., fuels (e.g., sterno, lighters), toilet bowl rings, lubricants, greases, wire rope lubricant, joint and cable fillers, soldering flux, buffing compounds, crayons and markers, modeling clay, rust preventatives, printing inks, protective/removable coatings and jet inks.

BRIEF DESCRIPTION OF THE DRAWING

FIG. 1 is graphical representation of the effect of temperature on rheology for a gelled hydrocarbon of the invention.

DETAILED DESCRIPTION OF THE INVENTION

The present invention is directed to ester-terminated polyamides (ETPA) and a method of preparing a resinous composition (hereinafter, simply "a resin") comprising, in whole or part, ester-terminated polyamide. A resin comprising ETPA (an "ETPA resin") is useful as a gelling agent for hydrocarbons and other liquids, where the resultant gels are useful components in, for example, candles, cosmetic formulations and other products that can benefit from gel-like character.

As used herein, ETPA refers to molecules of the formula (1), wherein n, $R^1$, $R^2$ and $R^3$ are later defined herein.

(1)

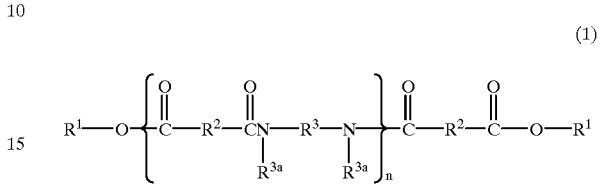

The inventive resin composition typically contains a mixture of ETPA molecules that may be characterized by the number of amide pairs present in the molecule, i.e., a portion of the resin may consist of ETPA molecules having a single amide pair, while another portion of the resin may consist of ETPA molecules having two amide pairs, etc. The amide pair distribution in the resin, by which is meant the proportion of the resin consisting of ETPA having zero, one, two or three, etc. amide pairs, depends in large part on the stoichiometry of the starting materials. The relationship between reactant stoichiometry and resin character will be discussed more fully below.

Thus, the invention is directed to an ester-terminated polyamide of the formula (1):

(1)

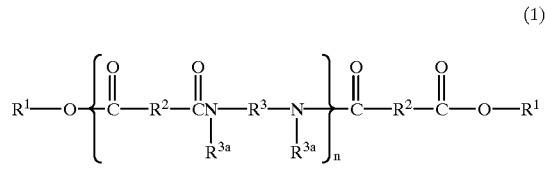

wherein n designates a number of repeating units such that ester groups constitute from 10% to 50% of the total of the ester and amide groups: $R^1$ at each occurrence is independently selected from an alkyl or alkenyl group containing at least 4 carbon atoms; $R^2$ at each occurrence is independently selected from a $C_{4-42}$ hydrocarbon group with the proviso that at least 50% of the $R^2$ groups have 30–42 carbon atoms; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen. For convenience, $R^1$, $R^2$, $R^3$ etc. will be referred to herein as "groups", however they could equally well be referred to as radicals ($R^1$) and diradicals ($R^2$ and $R^3$).

As may be seen from formula (1), the ester-terminated polyamides of the invention have ester groups, i.e., —C(=O)O— groups (which may equally well be written as —OC(=O)— groups) at both ends of a series of amide groups, i.e., —N($R^{3a}$)C(=O)— groups (which may equally well be written as —C(=O)N($R^{3a}$)— groups). The letter "n" designates the number of repeating units present in a molecule of ETPA, and is an integer greater than 0. According to the invention, n may be 1, in which case the ETPA contains equal amounts of ester and amide groups, i.e., the ester groups constitute 50% of the total of the ester and amide groups in the ETPA molecule. Preferably, the ETPA molecules are of relatively low molecular weight, so that n is preferably 1 to about 10, and more preferably is 1 to about 5. Because the ETPA molecules have such a low molecular weight, they could equally well be referred to as ester-terminated oligoamides. In any event, viewed another way, the ester groups constitute about 10% to about 50%, preferably about 15% to about 40%, and more preferably about 20% to about 35% of the total of the ester and amide groups. The invention is also directed to a mixture of ETPA molecules having various n values.

The $R^1$ group in formula (1) is an alkyl or alkenyl group which contains at least 4 carbon atoms. Alkyl groups are preferred, however alkenyl groups having 1–3, and preferably 1 site of unsaturation are also suitable. When ETPA molecules are made wherein $R^1$ has 4 or less carbon atoms, the ETPA molecule is a very poor gellant for pure hydrocarbon, particularly pure aliphatic hydrocarbon. However, it has been surprisingly found that when the number of carbon atoms in the $R^1$ group is increased above 4, and preferably has at least about 10 carbon atoms, more preferably at least about 12 carbon atoms, then the ETPA molecule and blends thereof are an excellent gellant for aliphatic hydrocarbon. The upper range for the number of carbon atoms in the $R^1$ group is not particularly critical however preferably the $R^1$ group has less than or equal to about 24 carbon atoms and more preferably has less than or equal to 22 carbon atoms. $R^1$ groups having about 16–22 carbon atoms are highly preferred. The identity of $R^1$ at any occurrence is independent of the identity of $R^1$ at any other occurrence.

The $R^2$ group in formula (1) is a hydrocarbon containing 4 to 42 carbon atoms. A preferred $R^2$ group contains 30–42 carbon atoms (i.e., is a $C_{30-42}$ group), and in fact at least 50% of the $R^2$ groups in an ETPA molecule or mixture of ETPA molecules according to the invention have 30–42 carbon atoms. Such $R^2$ groups are readily introduced into an ETPA molecule when the molecule is prepared from polymerized fatty acid, also known as dimer acid. Polymerized fatty acid is typically a mixture of structures, where individual dimer acids may be saturated, unsaturated cyclic, acyclic, etc. Thus, a detailed characterization of the structure of the $R^2$ groups is not readily available. However, good discussions of fatty acid polymerization may be found in, e.g, U.S. Pat. No. 3,157,681 and Naval Stores—Production, Chemistry and Utilization, D. F. Zinkel and J. Russel (eds.), Pulp. Chem. Assoc. Inc., 1989, Chapter 23.

Typical unsaturated fatty acids used to form polymerized fatty acid include oleic acid, linoleic acid, linolenic acid, etc. Tall oil fatty acid, which is a mixture containing long-chain unsaturated fatty acids obtained as a byproduct of the wood pulping process, is preferred for preparing polymerized fatty acid useful in the invention. While tall oil fatty acid is a preferred source of long-chain fatty acid, the polymerized fatty acid may alternatively be prepared by polymerization of unsaturated fatty acids from other sources, e.g., soybeans or canola. The $R^2$ group containing 30–42 carbon atoms may thus be described as having the structure of dimer or trimer acid, after removal of the carboxylic acid groups (as seen below, the carboxylic acid groups of dimer acid can react to form the amide and/or ester groups of the ETPA molecules).

While the ETPA molecules of the invention contain at least 50% $C_{30-42}$ groups as the $R^2$ group, preferably the total of the $R^2$ groups consist of at least 75% $C_{30-42}$ groups, and more preferably consist of at least 90% $C_{30-42}$ groups. An ETPA molecule, and mixture of ETPA molecules. wherein $R^2$ is entirely $C_{30-42}$ are preferred embodiments of the invention.

However, ETPA molecules may also contain $R^2$ groups having less than 30 carbon atoms. For example, an ETPA molecule of the invention may contain one or more $R^2$ groups having about 4 to 19, preferably about 4 to 12, and more preferably about 4 to 8 carbon atoms. The carbon atoms may be arranged in a linear, branched or cyclic fashion, and unsaturation may be present between any two carbon atoms. Thus. $R^2$ may be aliphatic or aromatic. When present, these lower carbon-number $R^2$ groups are preferably formed entirely of carbon and hydrogen, i.e., are hydrocarbon groups. Such lower carbon-number $R^2$ groups preferably constitute less than 50% of the $R_2$ groups; however, when present, constitute about 1% to about 50%. and preferably about 5% to about 35% of the total of the $R^2$ groups. The identity of $R^2$ at each occurrence is independent of the identity of $R^2$ at any other occurrence.

The $-N(R^{3a})-R^3-N(R^{3a})-$ group in formula (1) links two carbonyl (C=O) groups. In a preferred embodiment of the invention, all of the $R^{3a}$ groups in an ETPA molecule are hydrogen, so that $R^3$ alone joins the two nitrogen atoms shown in the formula $-N(R^{3a})-R^3-N(R^{3a})-$. In this case, the $R^3$ group contains at least two carbon atoms, and optionally oxygen and/or nitrogen atoms, in addition to hydrogen atoms necessary to complete otherwise unfilled vacancies of the carbon, oxygen and nitrogen atoms. In a preferred embodiment, $R^3$ is a hydrocarbon group, having 2 to about 36 carbon atoms, preferably having 2 to about 12 carbon atoms, and more preferably having 2 to about 8 carbon atoms. These carbon atoms may be arranged in a linear, branched or cyclic fashion, and unsaturation may be present between any two of the carbon atoms. Thus, $R^3$ may contain aliphatic or aromatic structures. The identities of $R^3$ and $R^{3a}$ at each occurrence are independent of their indentities at any other occurrence.

The $R^3$ groups may contain oxygen and/or nitrogen in addition to carbon and hydrogen atoms. A typical oxygen atom-containing $R^3$ group is a polyalkylene oxide, i.e., a group having alternating alkylene groups and oxygen atoms. Indeed, the oxygenation in a $R^3$ group is preferably present as an ether group. Representative polyalkylene oxides include, without limitation, polyethylene oxide, polypropylene oxide and copolymers (either random or block) of ethylene oxide and propylene oxide. Such oxygenated $R^3$ groups are readily introduced into an ETPA molecule of the invention through use of JeffamineTm diamines (Texaco, Inc., Houston, Tex.). These materials are available in a wide range of molecular weights. While some of the $R^3$ groups may contain oxygen (i.e., at least about 1%), preferably a minor number (i.e., less than 50%) of the $R^3$ groups contain oxygen, and more preferably less than about 20% of the $R^3$ groups contain oxygen. The presence of oxygen-containing $R^3$ groups tend to lower the softening point of the ETPA.

When present the nitrogen atoms in an $R^3$ group are preferably present as secondary or tertiary amines. A typical nitrogen atom-containing $R^3$ group having secondary amine groups is a polyalkylene amine, i.e., a group containing alternating alkylene groups and amine groups, and sometimes referred to as a polyalkylene polyamine. The alkylene group is preferably a lower alkylene group. e.g., methylene. ethylene, (i.e., $-CH_2CH_2-$), propylene etc. A typical polyalkylene amine may be represented by the formula $-NH-(CH_2CH_2NH)_mCH_2CH_2-NH-$ wherein m is an integer from 1 to about 5.

However, the nitrogen atoms in the nitrogen-containing $R^3$ group may alternatively (or additionally) be present as tertiary nitrogen atoms, e.g., they may be present in a heterocycle of the formula:

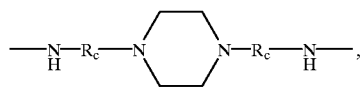

wherein $R_c$ is a $C_{1-3}$ alkyl group.

In the above-described nitrogen atom-containing $R^3$ groups, $R^{3a}$ was hydrogen. However, $R^{3a}$ need not be limited to hydrogen. In fact, $R^{3a}$ may be a $C_{1-10}$ alkyl group, preferably a $C_{1-5}$ alkyl group, and more preferably a $C_{1-3}$ alkyl group. In addition, $R^3$ and $R^{3a}$, or two $R^{3a}$ groups, may together form a heterocyclic structure, e.g., a piperazine structure such as

In this case, the two $R^{3a}$ groups may be seen as joining together to form an ethylene bridge between the two nitrogen atoms, while $R^3$ is also an ethylene bridge.

The invention also provides for a composition ("a resin") comprising the ETPA molecules as described above. Such a resin includes the ETPA molecules of formula (1) in addition to, for example, by-products that are formed during the ETPA-forming reaction. While the ETPA molecules of formula (1) may be purified from such by-products using, e.g., chromatography or distillation, the by-products are typically either minimal in amount or impart desirable properties to the resin, and thus need not be separated from the ETPA molecules of formula (1).

As described below, alcohols, amines and carboxylic acids are preferred starting materials to form the ETPA molecules and resins of the invention. These starting materials are preferably reacted together with a stoichiometry, and under reaction conditions, such that the acid number of the resulting resin is less than 25, preferably less than 15, and more preferably less than 10, while the amine number is preferably less than 10, more preferably less than 5, and still more preferably less than 1. The softening point of the resin is preferably greater than room temperature, more preferably is about 50° C. to about 150° C., and still more preferably is about 80° C. to about 130° C.

When the reactants and stoichiometry of the ETPA-forming reaction described below are properly chosen, some material of formula (1) wherein n=0, i.e., diester, can be formed. In a preferred embodiment of the invention, material of formula (1) wherein n=0 is present in the ETPA resin. A preferred resin of the invention contains from 50% to 70% ester groups, based on the total of the amide and ester groups in molecules of formula (1) (wherein n may be 0) present in the resin. Such a resin could also be produced by preparing ETPA as described above (having little or no n=0 material), and then preparing diester of formula (1) (n=0 exclusively, having no amide groups) in a separate reaction, and mixing the two materials together According to the present invention, monoalcohol, diacid including polymerized fatty acid, and diamine may be reacted to yield the ETPA resin. The resin is preferably characterized in that further reaction time does not provide for any significant change in the properties of the resin, i.e., the ETPA resin of the invention is substantially at reaction equilibrium. Each of the necessary reactants (monoalcohol, diacid and diamine) will now be described in turn, followed by a discussion of optional reactants and exemplary reaction conditions for preparing ETPA resin of the invention.

The monoalcohol is represented by the formula $R^1$—OH, wherein $R^1$ is a hydrocarbon group having at least four carbon atoms. Thus, the monoalcohol can also be described as a monohydric alcohol. $R^1$ is preferably a $C_{10-36}$ hydrocarbon, more preferably a $C_{12-24}$ hydrocarbon, still more preferably is a $C_{16-22}$ hydrocarbon, and yet still more preferably is a $C_{18}$ hydrocarbon. As used herein, the term $C_{10-36}$ refers to a hydrocarbon group having at least 10, but not more than 36 carbon atoms, and similar terms have an analogous meaning. The carbon atoms of the hydrocarbon group may be arranged in a linear, branched or cyclic fashion and the group may be saturated or unsaturated. However, $R^1$ is preferably linear, with the hydroxyl group located on a terminal carbon atom, i. e., the monoalcohol is a primary monoalcohol. Thus, 1-dodecanol, 1-tetradecanol, 1-hexadecanol (cetyl alcohol), 1-octadecanol (stearyl alcohol), 1-eicosanol (arachidyl alcohol) and 1-docosanol (behenyl alcohol) are preferred monoalcohols for preparing resins of the invention, where names in parentheses are common or trivial names by which these monoalcohols are known. While the monoalcohol has been exemplified with saturated alkyl groups, the monoalcohol may alternatively contain an alkenyl group, i.e., an alkyl group having unsaturation between at least any two adjacent carbon atoms. One or a mixture of these alcohols may be used to prepare a resin of the invention.

Another monoalcohol reactant suited for the invention is a so-called Guerbet alcohol. Guerbet alcohols have the general formula H—C(Ra)(Rb)—$CH_2$—OH wherein Ra and Rb may be the same or different and preferably represent a $C_{6-12}$ hydrocarbon group. Further discussion of Guerbet alcohols may be found in, e.g., "Dictionary For Auxiliaries For Pharmacy, Cosmetics And Related Fields," H. P. Fiedler, 3rd Ed., 1989, Editio Cantor Aulendorf. 2-Hexadecyloctadecanol, which has 24 carbon atoms, is a preferred Guerbet alcohol for use in the present invention.

Because $R^1$ is a hydrocarbon, the monoalcohol is a monofunctional reactant under the reaction conditions employed to prepare the resin of the invention (as discussed later). Furthermore, under preferred reaction conditions, $R^1$—OH is the only monoftmctional reactant used to form the inventive resin. Thus, a reactant mixture useful in preparing ETPA resin preferably does not contain monocarboxylic acid (i.e., an organic molecule containing a single carboxylic acid group) and/or monoamine (i.e., an organic molecule containing a single amine group).

The diacid is represented by the formula HOOC—$R^2$—COOH, and may therefore be referred to as a dicarboxylic acid, a dibasic acid or a dibasic carboxylic acid. $R^2$ is a hydrocarbon group where the carbon atoms thereof may be arranged in a linear, branched or cyclic fashion, and the group be saturated or unsaturated. In one embodiment of the invention, the diacid is exclusively polymerized fatty acid.

Polymerized fatty acid as used to form the resin of the invention is a well known and venerable material of commerce, and thus need not be described in great detail. Polymerized fatty acid is typically formed by heating long-chain unsaturated fatty acids, e.g, $C_{18}$ monocarboxylic acids, to about 200–250° C. in the presence of a clay catalyst in order that the fatty acids polymerize. The product typically comprises dimer acid, i.e., $C_{36}$ dicarboxylic acid formed by dimerization of the fatty acid, and trimer acid, i.e., $C_{54}$ tricarboxylic acid formed by trimerization of the fatty acid. Polymerized fatty acid is typically a mixture of structures, where individual dimer acids may be saturated, unsaturated, cyclic, acyclic, etc. A more detailed discussion of fatty acid polymerization may be found in. e.g., U.S. Pat. No. 3,157,681 and Naval Stores-Production, Chemistry and Utilization, D. F. Zinkel and J. Russell (eds.), Pulp. Chem. Assoc. Inc., 1989, Chapter 23.

Because fatty acid polymerization typically forms much more dimer acid than trimer acid, those skilled in the art may often refer to polymerized fatty acid as dimer acid even though some trimer acid, and even higher polymerization products, may be present with the dimer acid. It is preferred that the polymerized fatty acid contain less than about 10 weight percent of trimer acid, based on the total weight of the polymerized fatty acid, and that the dimer acid constitute at least about 90 weight percent of the polymerized fatty acid. More preferably, the dimer acid constitutes essentially all of the polymerized fatty acid.

Typical unsaturated fatty acids used to form polymerized fatty acid include oleic acid, linoleic acid, linolenic acid, etc. Tall oil fatty acid, which is a mixture containing long-chain unsaturated fatty acids obtained as a byproduct of the wood pulping process, is preferred for preparing polymerized fatty acid useful in the invention. While tall oil fatty acid is a preferred source of long-chain fatty acid, the polymerized fatty acid may alternatively be prepared by polymerization of unsaturated fatty acids from other sources, e.g., soybeans or canola. The polymerized fatty acid useful in the invention is a liquid, with an acid number on the order of about 180 to about 200.

The polymerized fatty acid of the invention may be hydrogenated prior to being used in the resin-forming reaction of the invention. Hydrogenation tends to provide for a slightly higher melting point for the inventive resin, as well as provide the resin with greater oxidative and color stability. Hydrogenated polymerized fatty acid tends to provide for a lighter colored resin, and is a preferred polymerized fatty acid for use in the practice of the present invention.

Polymerized fatty acid, dimer acid, and hydrogenated versions thereof may be obtained from a number of commercial suppliers. For example, Union Camp Corporation (Wayne, N.J.) sells polymerized fatty acid under their UNIDYME® trademark.

In another embodiment of the invention, the diacid used to prepare the ETPA resin is a mixture of polymerized fatty acid and "co-diacid," where the term co-diacid simply refers to any diacid of formula HOOC—$R^2$—COOH (where $R^2$ is defined above) excluding polymerized fatty acid. An exemplary co-diacid is a so-called "linear" diacid of the formula HOOC—$R^2$—COOH wherein $R^2$ is a linear $C_{4-12}$ hydrocarbon group, and more preferably is a linear $C_{6-8}$ hydrocarbon group. Linear diacids suitable for the present invention include 1,6-hexanedioic acid (adipic acid), 1,7-heptanedioic acid (pimelic acid), 1,8-octanedioic acid (suberic acid), 1,9-nonanedioic acid (azelaic acid), 1,10-decanedioic acid (sebacic acid), 1,11-undecanedoic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid).

Another exemplary co-diacid for use in the present invention is the reaction product of acrylic or methacrylic acid (or the ester thereof, with a subsequent hydrolysis step to form an acid) and an unsaturated fatty acid. For example, a $C_{21}$ diacid of this type may be formed by reacting acrylic acid with a $C_{18}$ unsaturated fatty acid (e.g., oleic acid), where an ene-reaction presumably occurs between the reactants. An exemplary $C_{21}$ diacid is commercially available from Westvaco Corporation, Chemical Division, Charleston Heights, S.C., as their product number 1550.

Aromatic diacids may be used as the co-diacid. An "aromatic diacid" as used herein is a molecule having two carboxylic acid groups (—COOH) or reactive equivalents thereof (e.g., acid chloride (—COCl) or ester (—COOR)) and at least one aromatic ring ("Ar"). Phthalic acids e.g., isophthalic acid and terephthalic acid, are exemplary aromatic diacids. The aromatic diacid may contain aliphatic carbons bonded to the aromatic ring(s), as in HOOC—$CH_2$—Ar—$CH_2$—COOH and the like. The aromatic diacid may contain two aromatic rings, which may be joined together through one or more carbon bonds, (e.g., biphenyl with carboxylic acid substitution) or which may be fused (e.g., naphthalene with carboxylic acid substitution).

The diamine reactant has two amine groups, both of which are preferably primary amines, and is represented by the formula HN($R^{3a}$)—$R^3$—N($R^{3a}$)H. $R^{3a}$ is preferably hydrogen, but may also be an alkyl group or may also join together with $R^3$ or another $R^{3a}$ to form a heterocyclic structure. Diamines wherein $R^{3a}$ is not hydrogen, and/or wherein $R^3$ is not a hydrocarbon, may be referred to herein as co-diamines. When present, co-diamines are preferably used in a minor amount compared to the diamines. $R^3$ may be a hydrocarbon group having at least two carbon atoms, where the carbon atoms may be arranged in a linear, branched or cyclic fashion, and the group may be saturated or contain unsaturation. Thus, $R^3$ may be aliphatic or aromatic. Preferred $R^3$ hydrocarbon groups have 2 to 36 carbon atoms, more preferred $R^3$ hydrocarbon groups have 2 to 12 carbon atoms. and still more preferred hydrocarbon groups have 2 to 6 carbon atoms.

Exemplary diamines having hydrocarbon $R^3$ groups, which are commercially available include, without limitation, ethylenediamine (EDA), 1,2-diaminopropane. 1,3-diaminopropane, 1,4-diaminobutane, 1,2-diamino-2-methylpropane, 1,3-diaminopentane, 1,5-diaminopentane, 2,2-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexanediamine, 1,9-diaminononane, 1,10-diaminodecane, 1,12-diaminododecane, diaminophenanthrene (all isomers, including 9,10), 4,4'-methylenebis (cyclohexylamine), 2,7-diaminofluorene, phenylene diamine (1,2; 1,3 and/or 1,4 isomers), adamantane diamine, 2,4,6-trimethyl-1,3-phenylenediamine, 1,3-cyclohexanebis (methylamine), 1,8-diamino-p-menthane, 2,3,5,6-tetramethyl-1,4-phenylenediamine, diaminonaphthalene (all isomers, including 1,5; 1,8; and 2,3) and 4-amino-2,2,6,6-tetramethylpiperidine.

Suitable aromatic diamines (by which is meant molecules having two reactive, preferably primary amine groups (—$NH_2$) and at least one aromatic ring ("Ar") include xylene diamine and naphthalene diamine (all isomers).

The $R^3$ group of the diamine may contain oxygen atoms in the form of a polyalkylene oxide group, in which case the diamine may be referred to as a co-diamine. Exemplary polyalkylene oxide-based co-diamines include, without limitation, the JEFFAMINE™ diamines, i.e., poly (alkyleneoxy)diamines from Texaco, Inc. (Houston, Tex.), also known as polyether diamines. Preferred polyalkylene oxide-containing co-diamines are the JEFFAMINE® ED and D series diamines. Ether-containing $R^3$ groups are not preferred, as they tend to lower the melting point of the resin to an undesirable extent. However, small amounts of a polyalkylene oxide-based diamine with a major amount of hydrocarbon-based diamine are well-suited for use in the invention. In general, the diarnine reactant may be a pure diamine as described above, or a mixture of such diamines.

The $R^3$ group of the diamine may contain nitrogen atoms, where these nitrogen atoms are preferably secondary or tertiary nitrogen atoms. A typical nitrogen atom-containing $R^3$ group having secondary nitrogen atoms is a polyalkylene amine, i.e., a group containing alternating alkylene groups and amine groups (i.e., —NH-groups). The alkylene group is preferably ethylene. i.e., —$CH_2CH_2$—, and the polyalkylene amine may be represented by the formula $NH_2$—$(CH_2CH_2NH)_mCH_2CH_2$—$NH_2$ wherein m is an integer from 1 to about 5. Diethylenetriamine (DETA) and triethylenetetraamine (TETA) are representative examples. When the diamine contains two primary amines in addition to secondary amines, the ETPA-forming reaction is preferably conducted at relatively low temperature, so that the primary amines (in preference to the secondary amines) react with the diacid component.

However, the nitrogen atoms in the nitrogen-containing $R^3$ group may also be present as tertiary nitrogen atoms, e.g., they may be present in a heterocycle of the formula:

wherein $R_c$ is a $C_{1-3}$ alkyl group. Bis(aminoethyl)-N,N'-piperazine and bis(aminopropyl)-N,N'-piperazine may be used to introduce these $R^3$ groups into an ETPA molecule, and these are such co-diamines according to the invention. In addition, the co-diamine may have one primary amine group and one secondary amine group (e.g., N-ethylethylenediamine or 1-(2-aminoethyl)piperazine). Generally, it is preferred that amine compounds having secondary amines not be present in the reaction mixture to any great extent, because their incorporation into an ester terminated polyamide tends to provide for poorer gelling ability of the ester-terminated polyamide.

In general, the diamine reactant may have the formula $HN(R^{3a})$—$R^3$—$NH(R^{3a})$ wherein $R^{3a}$ is preferably hydrogen, but may also be $C_{1-10}$alkyl, preferably $C_{1-5}$alkyl, and more preferably $C_{1-3}$alkyl. In addition, $R^{3a}$ may join together with $R^3$ or ;another $R^{3a}$ group to form a heterocyclic structure. For example, when piperazine is used as a co-diamine, the two $R^{3a}$ groups in the $HN(R^{3a})$—$R^3$—$NH(R^{3a})$ structure have joined together to form an ethylene bridge.

Reactive equivalents of diacids and/or diamines may be used in the invention. For example, diesters may be substituted for some or all of the diacid, where "diesters" refer to the esterification product of diacid with hydroxyl-containing molecules. However, such diesters are preferably prepared from relatively volatile hydroxyl-containing molecules, in order that the hydroxyl-containing molecule may be easily removed from the reaction vessel subsequent to monoalcohol and/or diamine (both as defined herein) reacting with the diester. A lower alkyl diester, e.g., the esterification or diesterification product of diacid as defined herein and a $C_{1-4}$ monohydic alcohol (e.g., methanol, ethanol, propanol and butanol), may be used in place of some or all of the diacid in the ETPA-resin forming reaction of the invention. The acid halide of the diacid may likewise be employed in place of some or all of the diacid. however such a material is typically much more expensive and difficult to handle compared to the diacid, and thus the diacid is preferred.

Likewise, the monoalcohol may be esterified with a volatile acid, e.g., acetic acid, prior to being employed in the ETPA resin-forming reaction of the invention. While such reactive equivalents may be employed in the reaction, their presence is not preferred because such equivalents introduce undesired reactive groups into the reaction vessel.

In preparing a resin of the invention the above-described reactants may be combined in any order. Preferably, the reactants are simply mixed together and heated for a time and at a temperature sufficient to achieve essentially complete reaction, to thereby form the inventive resin. The terms "complete reaction" and "reaction equilibrium" as used herein have essentially the same meaning, namely that further heating of the product resin does not result in any appreciable change in the performance characteristics of the product resin, where the most relevant performance characteristic is the ability of the product resin to form a clear, firm gel upon being combined with a liquid hydrocarbon (as mentioned above and discussed further below).

Thus, the ETPA resin may be formed in a one-step procedure, wherein all of the monoalcohol, diacid (including co-diacid) and diamine (including co-diamine) are combined and then heated to about 200–250° C. for a few hours, typically 2–8 hours. As one or more of the reactants may be a solid at room temperature, it may be convenient to combine each of the ingredients at a slightly elevated temperature, and then form a homogeneous mixture prior to heating the reaction mixture to a temperature sufficient to cause reaction between the monoalcohol, diacid and diamine. Alternatively, although less preferably, two of the reactants may be combined and reacted together, and then the third reactant is added followed by further heating the desired product is obtained. Reaction progress may be conveniently monitored by periodically measuring the acid and/or amine number of the product mixture. As one example, the diacid may be reacted with the diamine so as to form polyamide, and then this intermediate polyamide may be reacted with monoalcohol to form ester-terminated polyamide. Or, the diacid may be reacted with the monoalcohol to thereby form diester, and this diester may be reacted with diamine to thereby form ester-terminated polyamide. Because the components of the product resin are preferably in reaction equilibrium (due to transamidation and transesterification reactions), the order in which the reactants are combined preferably does not impact on the properties of the ETPA resin.

Any catalyst that may accelerate amide formation between carboxylic acid and arnine groups, and/or ester formation between carboxylic acid and hydroxyl groups, may be present in the reaction mixture described above. Thus, mineral acid such as phosphoric acid, or tin salts such as dibutyltin oxide, may be present during the reaction. In addition, it is preferred to remove water from the reaction mixture as it is formed upon amide and ester formation. This is preferably accomplished by maintaining a vacuum on the reacting mixture.

It is important to control the stoichiometry of the reactants in order to prepare ester-terminated polyamide according to the invention. In the following discussion regarding reactant stoichiometry, the terms "equivalent(s)" and "equivalent percent" will be used, and are intended to have their standard meanings as employed in the art. However, for additional clarity, it is noted that equivalents refer to the number of reactive groups present in a molar quantity of a molecule, such that a mole of a dicarboxylic acid (e.g., sebacic acid) has two equivalents of carboxylic acid, while a mole of monoalcohol has one equivalent of hydroxyl. Furthermore, it is emphasized that the diacid has only two reactive groups (both carboxylic acids), the monoalcohol has only one reactive group (a hydroxyl group) and the diamine has only two reactive groups (preferably both primary amines), and these are preferably, although not necessarily, the only reactive materials present in the reaction mixture.

According to the invention, is it preferred that the equivalents of carboxylic acid are substantially equal to the combined equivalents of hydroxyl contributed by monoalcohol and amine contributed by diamine. In other words, if the reaction mixture used to form an ETPA resin has "x" equivalents of carboxylic acid, "y" equivalents of amine and "z" equivalents of hydroxyl, then $0.9 \leq \{x/(y+z)\} < 1.1$, and preferably $\{x/(y+z)\}$ is substantially 1.0. Under these conditions, substantially all of the carboxylic acid groups will react with substantially all of the hydroxyl and amine groups, so that the final product contains very little unreacted carboxylic acid, hydroxyl or amine groups. In other words, each of the acid and amine numbers of a resin of the invention is preferably less than about 25, is more preferably less than about 15, and is more preferably less than about 10, and is still more preferably less than about 5.

When co-diacid is employed to prepare an ETPA resin, the co-diacid preferably contributes no more than about 50% of the equivalents of carboxylic acid present in the reaction mixture. Stated another way, the co-diacid contributes from 0–50 equivalent percent of the acid equivalents in the reaction mixture. Preferably, the co-diacid contributes 0–30 equivalent percent, and more preferably contributes 0–10 equivalent percent of the acid equivalents in the reaction mixture.

When co-diamine is employed to prepare an ETPA resin, the co-diamine present in the reaction mixture. Stated another way, the co-diamine contributes from 0–50 equivalent percent of the amine equivalents in the reaction mixture. Preferably, the co-diamine contributes 0–30 equivalent percent, and more preferably contributes 0–10 equivalent percent of the amine equivalents in the reaction mixture.

In order to prepare the resin of the invention, it is important to control the relative equivalents of hydroxyl and amine used in the resin-forming reaction. Thus, hydroxyl groups contribute about 10–70% of the total equivalents of hydroxyl and amine employed to prepare an ester-terminated polyamide-containing resin of the invention. Stated another way, $0.1 \leq \{z/(y+z)\} \leq 0.7$, where y and z have been defined above. In a preferred embodiment, $0.2 \leq \{z/(y+z)\} \leq 0.5$, while in a further preferred embodiment, $0.25 \leq \{z/(y+z)\} \leq 0.4$.

The stoichiometry of the reactants will have a significant impact on the composition of the ETPA resin. For example, ETPA resins made with increasing amounts of monoalcohol will tend to have lower average molecular weights. In other words, as more monofunctional reactant is used, the number of amide pairs in an average ETPA molecule of the resin will tend to decrease. In fact, when 70 equivalent percent monoalcohol is employed, the majority of the ETPA molecules in the resin will have only one or two amide pairs. On the other hand, as less monoalcohol is used, the average molecular weight of the ETPA in the resulting resin will increase. In general, increasing the average molecular weight for the ETPAs in a resin will tend to increase the melting point and melt viscosity of the resin, which tends to provide a firmer gel when the ETPA resin is combined with a low polarity liquid.

As stated above, the ester-terminated polyamides described herein are useful in forming gels with liquid hydrocarbons (as well as other liquids) at room temperature, and accordingly preferably have a softening point greater than room temperature. A precise definition of "gel" is not easy to give, although most if not all researchers recognize a "gel." Generally, a gel is more viscous than a liquid or paste, and retains its shape when left undisturbed, i.e., is self-supporting. However, a gel is not as hard or firm as a stick or wax. Gels may be penetrated more easily than a wax-like solid, where "hard" gels are relatively more resistant to penetration than "soft" gels.

Almdale et al. (Polymer Gels and Networks, Vol. 1, No. 5 (1993)) list two criteria for defining a system as a gel: (1) a gel consists of two or more components, one of which is a liquid, present in substantial quantities; and (2) a gel is a soft material which is solid or solid-like. This latter requirement can be described more accurately through rheological measurement. Typically, gels possess a storage modulus G'(w) which exhibits a pronounced plateau at higher frequencies (on the order of 1–100 radians/second), and a loss modulus G"(w) which is considerably smaller than the storage modulus in the plateau region. In a strict sense, the term "gel" applies to systems having a value G'(w) that is higher than its value of G"(w) at low frequencies. Many of the compositions according to the present invention are gels by one or both of the above definitions. A gel is free-standing or self-supporting in that its yield value is greater than the sheer stress imposed by gravity.

Rheological parameters such as the storage modulus G'(w) can be measured as a function of angular frequency with a parallel-plate rheometer. For example, such parameters can be generated using a Rheometrics Dynamic Analyzer Model 70, using a 0.5 cm stainless steel plate and a 2.3 mm sample gap, over a temperature sweep of 25–85° C. at 1% strain and 6.3 radians/sec. A characterization of the rheological behavior of a gel according to the present invention was made using the Rheometrics instrument and conditions set forth above. The gel was prepared according to Example 3 set forth herein. As demonstrated by FIG. 1, the elastic modulus (G') is 5–10 fold greater than the loss modulus (G") at room temperature for this composition, thus demonstrating that a gel structure is present. As the gel is heated, it retains significant gel-like character at least up to about 50° C. However, as the gel is further heated, and the melting point of the ester-terminated polyamide resin is reached. the loss modulus will eventually equal the storage modulus (i.e., tan δ equals 1), and the composition loses its gel-like character (at a temperature of about 65–70° C., based on extrapolation of the data in FIG. 1).

A commercially desirable aspect of the invention is that the gel may be (although need not be) essentially transparent. Thus, the gels are desirably combined with colorants, as well as other ingredients, to form lipstick and other cosmetic products. The advantage of a clear gel in these applications is that the gel imparts little if any undesirable color to the lipstick or cosmetic. The gels may be combined with aluminum zirconium salts, as well as other ingredients, to form colorless underarm deodorant/antiperspirant, which is currently quite popular. The gels of the invention are also useful in other personal care products, e.g., cosmetics such as eye make-up, lipstick, foundation make-up, costume make-up, as well as baby oil, make-up removers, bath oil, skin moisturizers, sun care products, lip balm, waterless hand cleaner, medicated ointments, ethnic hair care products, perfume, cologne, and suppositories. In addition, the gels may be used in household products such as automobile wax/polish, candles, furniture polish, metal cleaners/polishes, household cleaners, paint strippers and insecticide carriers.

The gels may also be used in industrial products such as fuels (sterno, lighters), toilet bowl rings, lubricants/greases, wire rope lubricant, joint and cable fillers, soldering flux, buffing compounds, crayons and markers, modeling clay, rust preventatives, printing inks, protective/removable coatings, and jet inks. For example, hydrocarbon gelled with an ETPA resin of the invention may be used as a heat source in, e.g., a cooking apparatus used in camping and hiking. Such a composition will not flow if tilted, and thus may be safer and neater than similar products made from flowing materials.

Formulations to prepare such materials are well known in the art. For example, U.S. Pat. Nos. 3,615,289 and 3,645,705 describe the formulation of candles. U.S. Pat. Nos. 3,148,125 and 5,538,718 describe the formulation of lipstick and other cosmetic sticks. U.S. Pat. Nos. 4,275,054, 4,937,069, 5,069,897, 5,102,656 and 5,500,209 each describe the formulation of deodorant and/or antiperspirant. Each of these U.S. Patents is hereby incorporated fully herein by reference.

The ETPA resin of the invention may be incorporated into commercial products such as those listed above by blending the ETPA resin with the other components of the product. Typically, the ETPA resin will be present at a concentration of about 1% to about 50% of the composition, based on the total weight of the composition. It is a routine matter to optimize the amount of ETPA resin to have present in a composition, and indeed the amount will vary depending on the actual product and the desired consistency of the product. In general, as more ETPA resin is used in a formulation, the product will display a more pronounced gel character.

Accordingly, another aspect of the invention is a gel formed between ingredients comprising ester-terminated polyamide as described above and a nonaqueous liquid, preferably a low-polarity liquid. A preferred low polarity liquid is a hydrocarbon, with preferred hydrocarbons being solvents and oils. Solvents and oils may be distinguished in that defatting occurs when solvents are rubbed on human skin, leading to drying and irritation. However, defatting does not occur when oils are rubbed on human skin. Oils are more preferred than solvents in most personal-care formulations, and thus are preferred in forming the gels of the present invention. Preferably, the hydrocarbon has a relatively high number of carbon atoms, e.g., 10 to 30 carbon atoms, and thus is not a volatile hydrocarbon.

A preferred oil is mineral oil, also sometimes referred to as medicinal oil. Mineral oil is a highly refined, colorless, tasteless, and odorless petroleum oil (i.e., derived by processing petroleum/crude oil) used medicinally as an internal lubricant and for the manufacture of salves and ointments. Such mineral oils are highly refined in having substantially all volatile hydrocarbons removed therefrom, and in being hydrogenated (also called hydrotreated) in order to remove substantially all unsaturation, e.g., aromatic groups have been reduced to the fully saturated analog. A preferred mineral oil to prepare a gel of the invention is so-called "white" mineral oil, which is water-white (i.e., colorless and transparent) and is generally recognized as safe for contact with human skin. Mineral oil may also be characterized in terms of its viscosity, where light mineral oil is relatively less viscous than heavy mineral oil, and these terms are defined more specifically in the U.S. Pharmacopoeia, $22^{nd}$ revision, p. 899 (1990). Any mineral oil may be used in the invention to form a gel.

Other hydrocarbons that may be used in the invention include relatively lower molecular weight hydrocarbons including linear saturated hydrocarbons such a tetradecane, hexadecane, octadecane, etc. Cyclic hydrocarbons such as decahydronaphthalene (DECALIN), fuel grade hydrocarbons, branched chain hydrocarbons such as PERMETHYL from Permethyl Corporation and ISOPAR from Exxon Corp., and hydrocarbon mixtures such as product PD-23 from Witco (Greenwich, Conn.) may also be used in preparing gels of the invention. Such hydrocarbons, particularly saturated hydrocarbon oils, are a preferred liquid for preparing a gel of the invention because such hydrocarbons are often less irritating to the skin than liquids containing aromatic, ketone and other functional groups.

Another class of suitable low polarity liquids are esters, and particularly esters of fatty acids. Such esters may be monofunctional esters (i.e., have a single ester moiety) or may be polyfunctional (i.e., have more than one ester group). Suitable esters include, but are not limited to, the reaction products of $C_{1-24}$ monoalcohols with $C_{1-22}$ monocarboxylic acids, where the carbon atoms may be arranged in a linear, branched and/or cyclic fashion, and unsaturation may optionally be present between carbon atoms. Preferably, the ester has at least about 18 carbon atoms. Examples include, but are not limited to, fatty acid esters such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate and tetratriacontanyl stearate; salicylates, e.g., $C_{1-10}$ salicylates such as octyl salicylate, and benzoate esters including $C_{12-15}$ alkyl benzoate, isostearyl benzoate and benzyl benzoate.

Suitable esters are those commonly employed in the cosmetics industry for the formulation of lipstick and make-up, e.g., the fatty acid esters mentioned above, and are often denoted as "cosmetic esters". Other cosmetic esters include glycerol and propylene glycol esters of fatty acids, including the so-called polyglycerol fatty acid esters and triglycerides. Exemplary cosmetic esters include, without limitation, propylene glycol monolaurate, polyethylene glycol (400) monolaurate, castor oil, triglyceryl diisostearate and lauryl lactate. Thus, the liquid may have more than one of ester, hydroxyl and ether functionality. For example, $C_{10-15}$ alkyl lactate may be used in a gel of the invention. In addition, esterified polyols such as the polymers and/or copolymers of ethylene oxide, propylene oxide and butylene oxide reacted with $C_{1-22}$ monocarboxylic acids are useful. The carbon atoms of the $C_{1-22}$ monocarboxylic acids may be arranged in a linear, branched and/or cyclic fashion, and unsaturation may be present between the carbon atoms. Preferred esters are the reaction product of an alcohol and a fatty acid, where the alcohol is selected from $C_{1-10}$ monohydric alcohol, $C_{2-10}$ dihydric alcohol and $C_{3-10}$ trihydric alcohol, and the fatty acid is selected from a $C_{8-24}$ fatty acid.

The gels of the invention preferably do not contain substantial amounts of monoalcohol, i.e., monohydric alcohols having a single hydroxyl and their only functional group. Thus, the gels of the invention preferably contain less than 25 weight percent, more preferably less than 10 weight percent, and still more preferably less than 5 weight percent of monoalcohol. It is a surprising advantage of the present invention that the ETPA resin can gel hydrocarbon in the absence of hydroxyl-containing compounds.

The gels of the invention are preferably self-supporting, in that they retain their shape at room temperature and in the absence of shear. Also, the inventive gels are preferably clear or translucent. The terms clear, transparent and clarity are intended to have their ordinary dictionary definitions;

thus, a clear gel allows ready viewing of objects behind it. By contrast, a translucent gel, although allowing light to pass through, causes the light to be so scattered that it will be impossible to see clearly objects behind the translucent stick. As used herein, a gel is transparent or clear if the maximum transmittance of light of any wavelength in the range 400 to 800 nm through a sample 1 cm thick is at least 35%, preferably at least 50% (see, e.g., European Patent Publication No. 291,334 A4). The gel is translucent if the maximum transmittance of such light through the sample is between 2% and less than 35%. The transmittance can be measured by placing a sample of the aforementioned thickness into a light beam of a spectrophotometer whose working range includes the visible spectrum, such as a Bausch & Lomb Spectronic 88 Spectrophotometer.

The gels of the invention preferably do not display syneresis. As defined in the McGraw-Hill Dictionary of Scientific and Technical Terms ($3^{rd}$ Edition), syneresis is the spontaneous separation of a liquid from a gel or colloidal suspension due to contraction of the gel. Typically, syneresis is observed as the separation of liquid from a gel, and is sometimes referred to as "bleeding", in that wetness is seen along the surfaces of a gel that displays syneresis. From a commercial point of view, syneresis is typically an undesirable property, and the gels of the present invention desirably, and surprisingly do not exhibit syneresis.

To prepare a gel of the invention, an ester-terminated polyamide resin is combined with a liquid. The two ingredients are taken to elevated temperature, e.g., up to about 80–150° C., until the resin completely dissolves in the liquid. A lower temperature may be used if a solution can be prepared at the lower temperature. Upon cooling, the mixture forms the gel of the invention. Preferably, the liquid is a low-polarity liquid as described above, and more preferably the liquid is a hydrocarbon. The liquid may contain more than one component, e.g., hydrocarbon as well as ester-containing material. In any event, the ester-terminated polyamide is combined with the liquid such that the weight percent of ETPA in the ETPA+solvent mixture is about 5–50%, and preferably is about 10–45%. Such gels may be transparent, translucent or opaque, depending on the precise identities of the ester-terminated polyamide and liquid, as well as the concentration of ETPA in the mixture.

The gels of the invention may be formulated into personal care products according to techniques well known in the art. The gel may be combined with ingredients conventionally incorporated into personal care products such as chelating agents, colorants, emulsifiers, fillers, hardeners, perfumes, strengtheners, water and wax, to name a few. Such additives are also set forth in, e.g., the following documents, all incorporated by reference herein in their entirety: U.S. Pat. Nos. 3,255,082 to Barton, 4,049,792 to Elsnau, 4,137,306 to Rubino et al., and 4,279,658 to Hooper et al., Personal care products may be prepared from the ETPA resin of the invention by mixing the various components of the product at an elevated temperature and then cooling in order to form the gelled (solidified) composition. Desirably, any volatile components are added to the mixture at a relatively late stage of the mixing, so as to limit volatilization of the component. Preferably, the liquid and ETPA gelling agent are mixed and heated so as to fully dissolve the ETPA in the liquid (e.g., at 80° C.–150° C.). An active ingredient (e.g., active antiperspirant) can be added after the ETPA fully dissolves, and mixing then takes place. Mixing may continue during cooling, with colorant or other component being added during the cooling stage.

The following examples are set forth as a means of illustrating the present invention and are not to be construed as a limitation thereon.

In the following Examples, softening point was measured using a Model FP83HT Dropping Point Cell from Mettler Instruments Corporation, with a heating rate of 1.5° C./min. Viscosity measurements were made using a Model RVTD Digital Viscometer from Brookfield Engineering Laboratories, Inc., and are reported in centipoise (cP). Gel clarity and hardness were both judged qualitatively.

In the synthesis Examples that follow, and unless otherwise noted, the chemicals were all of reagent grade, obtained from commercial supply houses including Aldrich Chemical Co. (Milwaukee, Wis.) and the like. Unidyme™ 14 polymerized fatty acid is a dimer acid available from Union Camp Corp., Wayne, N.J. Empol™ 1008 polymerized fatty acid is a dimer acid available from Henkel Corporation, Ambler, Pa. Pripol™ 1008 polymerized fatty acid is a dimer acid available from Unichema North America, Chicago, Ill. Harchemex™ (Union Camp Co., Wayne N.J.) alcohol is a 60/40 blend of $C_{14}/C_{16}$ linear alcohols.

EXAMPLES

EXAMPLE 1

ETPA From $C_{14}$–$C_{16}$ Linear Alcohol

This Example shows that a clear, soft gel can be made with an ETPA synthesized from a blend of linear alcohols having chain lengths of 14 and 16 carbons.

The components and amounts thereof as shown in Table 1 were charged to a reaction vessel and heated at 200–220° C. under a nitrogen atmosphere for 2 hours. The resulting ETPA had a softening point of 68.5° C. and a viscosity of 44 centipoise at 130° C., as summarized in Table 2.

TABLE 1

REACTANTS USED TO FORM A LINEAR $C_{14}/C_{16}$ ALCOHOL-TERMINATED POLYAMIDE

| Reactant | % Equivalents | Weight % |
| --- | --- | --- |
| Unidyme ™ 14 | 100 | 65.6 |
| Hexamethylene diamine | 50 | 6.5 |
| Harchemex | 50 | 27.8 |

This ETPA was combined with tetradecane (20 wt % ETPA/80 wt % tetradecane ) and heated until the ETPA dissolved in the tetradecane. Upon cooling to room temperature, the solution formed a soft clear gel, summarized in Table 2.

EXAMPLE 2

ETPA From $C_{22}$ Linear Alcohol

This example shows that a clear, soft gel can be made with an ETPA synthesized from a linear alcohol having a chain length of 22 carbons.

The starting materials used to prepare the ETPA are identified in Table 3 and the properties of the resulting ETPA are given in Table 2. The resin and the gel were made in the manner described in Example 1.

TABLE 3

REACTANTS USED TO FORM A LINEAR $C_{22}$ ALCOHOL-TERMINATED POLYAMIDE

| Reactants | % Equivalents | Weight % |
|---|---|---|
| Pripol ™ 1009 | 100 | 56.6 |
| Hexamethylene diamine | 40 | 4.6 |
| Behenyl alcohol | 60 | 38.8 |

EXAMPLE 3

ETPA From $C_{18}$ Linear Alcohol

This example shows that a clear, soft gel can be made with an ETPA synthesized from a linear alcohol having a chain length of 18 carbons.

Using the reactants identified in Table 4, an ETPA was synthesized by charging the diacid and alcohol to a reaction vessel at room temperature, heating the mixture under nitrogen to 80° C., adding the diamine, heating to 220° C., holding at 220° C. for 1 hour, and finally holding under vacuum (8–10 mbar) at 220° C. for 2 hours. As summarized in Table 2, the ETPA had a softening point of 85.7° C. and a viscosity at 190° C. of 27 cp.

TABLE 4

REACTANTS USED TO FORM A LINEAR $C_{18}$ ALCOHOL-TERMINATED POLYAMIDE

| Reactant | % Equivalents | Weight % |
|---|---|---|
| Empol ™ 1008 | 100 | 71.9 |
| Ethylene Diamine | 65 | 4.8 |
| Stearyl Alcohol | 35 | 23.3 |

A gel was formed from this ETPA according to the procedure described in Example 1. As characterized in Table 2, the gel was clear and hard.

EXAMPLE 4

ETPA From $C_{24}$ Branched-Chain Alcohol

This example shows that a clear, hard gel can be made with an ETPA synthesized from a branched alcohol having a chain size of 24 carbons.

An ETPA was synthesized according to the procedure described in Example 3, using the reactants as identified in Table 5. The resultant ETPA resin had a softening point of 85.2° C. and a viscosity of 20 cP at 190° C.

TABLE 5

REACTANTS TO FORM A BRANCHED $C_{24}$ ALCOHOL-TERMINATED POLYAMIDE

| Reactant | % Equivalents | Weight % |
|---|---|---|
| Empol ™ 1008 | 100 | 64.7* |
| Ethylene Diamine | 60 | 4.0 |
| Iso Tetracosanol | 40 | 31.3 |

A gel was prepared from this ETPA according to the procedure described in Example 1. As summarized in Table 2, the gel was clear and hard.

EXAMPLE 5

ETPA From $C_{10}$ Linear Alcohol

This example shows that an opaque gel in tetradecane is formed when an ETPA made from a linear alcohol having a chain length of 10 carbons is used.

The ETPA was synthesized in the manner described in Example 3 using the reactants identified in Table 6. As summarized in Table 2, the ETPA had a softening point of 93.2° C. and a viscosity at 190° C. of 29 cp.

TABLE 6

REACTANTS TO FORM A LINEAR $C_{10}$ ALCOHOL-TERMINATED POLYAMIDE

| Reactant | % Equivalents | Weight % |
|---|---|---|
| Empol ™ 1008 | 100 | 79.5 |
| Ethylene Diamine | 65 | 5.4 |
| n-Decanol | 35 | 15.1 |

This ETPA was combined with tetradecane to form a gel according to the procedure of Example 1. The gel was opaque and hard, as summarized in Table 2.

EXAMPLE 6

ETPA with moderate $C_4$ Linear Alcohol termination

This example shows that an opaque gel in tetradecane is formed when an ETPA made from a linear alcohol having a chain length of 4 carbons is used.

With one exception, the ETPA was synthesized in the manner described in Example 3, using the reactants set forth in Table 7. In this Example however, excess butanol was added to the formulation before the vacuum stage, to thereby reduce the acid number to 10–15. As summarized in Table 2, the gel had a softening point of 86.3° C. and a viscosity of 35 cp at 190° C.

TABLE 7

REACTANTS USED TO FORM A LINEAR $C_4$ ALCOHOL-TERMINATED POLYAMIDE

| Reactant | % Equivalents | Weight % |
|---|---|---|
| Empol ™ 1008 | 100 | 88.5 |
| Ethylene Diamine | 65 | 5.8 |
| n-Butanol | 35 | 7.7 |

A gel was made from this ETPA as described in Example 1. The gel was opaque and soft, and showed syneresis (i.e., "bleeding" of tetradecane from the gel), which is undesirable.

EXAMPLE 7

ETPA From with high $C_4$ Linear Alcohol termination

This example shows that a clear gel in tetradecane is formed when an ETPA made from a linear alcohol having a chain length of 4 carbons at a relatively high concentration (50% eq.) is used.

An ETPA was synthesized in the manner described in Example 6, again using excess butanol before the vacuum stage in order to reduce the acid number to 10–15. The reactants used to form this ETPA are set forth in Table 8. The product ETPA has a softening point of 77.2° C. and a viscosity of 15 cP at 190° C.

TABLE 8

REACTANTS USED TO FORM A LINEAR $C_4$ ALCOHOL-TERMINATED POLYAMIDE

| Reactant | % Equivalents | Weight % |
| --- | --- | --- |
| Empol ™ 1008 | 100 | 84.8 |
| Ethylene Diamine | 50 | 4.4 |
| n-Butanol | 50 | 10.8 |

A gel was made using this ETPA, according to the procedure described in Example 1. The gel was clear and hard (see Table 2).

EXAMPLE 8

ETPA From with low $C_{18}$ Linear Alcohol termination

This example shows that there is a lower limit to the alcohol concentration that can be used in an ETPA, and still obtain a transparent gel therefrom. Below this limit, opaque gels in tetradecane are formed.

An ETPA was synthesized according to the procedure of Example 3, using the reactants identified in Table 9. The ETPA has a softening point of 90.4° C. and a viscosity of 47 cp at 190° C.

TABLE 9

REACTANTS USED TO FORM A LINEAR $C_{18}$ ALCOHOL-TERMINATED POLYAMIDE

| Reactant | % Equivalents | Weight % |
| --- | --- | --- |
| Empol ™ 1008 | 100 | 76.4 |
| Ethylene Diamine | 75 | 5.9 |
| Stearyl alcohol | 25 | 17.7 |

This ETPA was formed into a gel according to the procedure outlined in Example 1. The gel was hard but opaque, as summarized in Table 2.

EXAMPLE 9

ETPA From with very high $C_{24}$ Branched-chain Alcohol termination

This example shows that a there is an upper limit to the alcohol concentration that can be used in a forming an ETPA, and still obtain a hard gel. Above this limit, clear, extremely soft gels in tetradecane are formed.

An ETPA was synthesized as in Example 1, using the reactants set forth in Table 10. The ETPA was very soft, having a melting point below room temperature. The viscosity of the ETPA at 130° C. was 20.5 cp.

TABLE 10

REACTANTS USED TO FORM A BRANCHED $C_{24}$ ALCOHOL-TERMINATED POLYAMIDE

| Reactant | % Equivalents | Weight % |
| --- | --- | --- |
| Empol ™ 1008 | 100 | 51.5 |
| Hexamethylene Diamine | 30 | 3.1 |
| Iso Tetracosanol | 70 | 45.4 |

A gel was prepared from this ETPA as described in Example 1. The gel was clear but very soft, as summarized in Table 2.

EXAMPLE 10

ETPA From co-diacid and $C_{18}$ Linear alcohol

This example shows that a co-diacid can be added to the ETPA formulation to increase the gel hardness while maintaining clarity.

An ETPA was synthesized as in Example 3, charging the co-diacid before heating. The reactants listed in Table 11 were used to form this ETPA. The product had a softening point of 133.5° C. and a viscosity at 190° C. of 26 cp.

TABLE 11

REACTANTS USED TO FORM A LINEAR $C_{18}$ ALCOHOL-TERMINATED POLYAMIDE WITH 10% SEBACIC ACID

| Reactant | % Equivalents | Weight % |
| --- | --- | --- |
| Empol ™ 1008 | 90 | 67.8 |
| Sebacic Acid | 10 | 2.7 |
| Ethylene Diamine | 65 | 5.1 |
| Stearyl alcohol | 35 | 24.4 |

Using the procedure of Example 1, a gel was formed from this ETPA. The gel was clear and hard, as summarized in Table 2.

TABLE 2

THE PHYSICAL AND GEL PROPERTIES OF ETPAs MADE FROM VARIOUS ALCOHOL SIZES AND CONCENTRATIONS

| Ex. No. | Alcohol Chain | Alc. Conc. (% eq.) | Soft. Pt. (° C.) | Viscosity (cP) | 20 wt % ETPA in tetradecane |
| --- | --- | --- | --- | --- | --- |
| 7 | 4 (linear) | 50 | 77.2 | 15 @ 190° C. | clear, hard gel |
| 6 | 4 (linear) | 35 | 86.3 | 35 @ 190° C. | opaque, soft gel, syneresis |
| 5 | 10 (linear) | 35 | 93.2 | 29 @ 190° C. | opaque, hard gel |
| 1 | 14, 16 (linear) | 50 | 68.5 | 44 @ 130° C. | clear, soft gel |
| 3 | 18 (linear) | 35 | 85.7 | 27 @ 190° C. | clear, hard gel |
| 8 | 18 (linear) | 25 | 90.4 | 47 @ 190° C. | opaque, hard gel |
| 10 | 18 (+10% sebacic) | 35 | 133.5 | 26 @ 190° C. | clear, hard gel |
| 2 | 22 (linear) | 60 | 73.1 | 36.5 @ 130° C. | clear, soft gel |
| 9 | 24 (branched) | 70 | ≈RT | 20.5 @ 130° C. | clear, very soft gel |
| 4 | 24 (branched) | 40 | 85.2 | 20 @ 190° C. | clear, hard gel |

EXAMPLE 11

Effect of Alcohol Chain Length on Gel Clarity

This Example shows that the chain length of the alcohol used to prepare an alcohol terminated polyamide, will have an affect on the clarity of the gel made from that polyamide. This Example further shows that the concentration of gellant in a hydrocarbon medium will affect the clarity of the gel.

The alcohol terminated polyamides of Example Nos. 6 ($C_4$ linear alcohol), 5 ($C_{10}$ linear alcohol) and 3 ($C_{18}$ linear alcohol) were dissolved in hot tetradecane at concentrations ranging from 10 to 30 wt % based on the total weight of ETPA and tetradecane. Upon cooling, the resulting gels were evaluated for clarity with the results as set forth in Table 12.

TABLE 12

GEL CLARITY AS A FUNCTION OF GELLANT CONCENTRATION AND THE CHAIN LENGTH OF THE ALCOHOL USED TO PREPARE THE GELLANT

| Example Number | Alcohol Chain Length | Wt % Gellant In Tetradecane + Gellant Mixture | | | |
|---|---|---|---|---|---|
| | | 10 | 15 | 20 | 30 |
| 6 | $C_4$ | Opaque | Opaque | Opaque | Opaque |
| 5 | $C_{10}$ | Opaque | Opaque | Opaque | Translucent |
| 3 | $C_{18}$ | Opaque | Clear | Clear | Clear |

The data of Table 12 shows that none of the ETPAs form clear gels at 10 wt % solids. At 15 wt. % and 20 wt. % gellant using tetradecane, only the stearyl alcohol-terminated polyamide forms clear gels.

EXAMPLE 12

Effect Of Hydrocarbon On Gel Hardness And Clarity

When the ETPAs of Example 11 were used to form gels in deca in, the gels showed improved clarity however tended to be softer. The clarity behavior described in Example 11 is essentially reproduced when tetradecane is replaced with isooctane or with PD 23 (a hydrocarbon blend from Witco, Corp., Greenwich, Conn.). In isooctane, a gel tends to be harder compared to when decalin is used, however softer than when tetradecane is used.

EXAMPLE 13

ETPA Composition Used For Gelling A Hydrocarbon Solvent

This example shows how an ETPA can be used to produce a clear, hard gel in PD 23 hydrocarbon, where PD 23 is a petroleum distillate made by Witco (Greenwich, Conn.) that has a viscosity of 2.6 cSt at 40° C. and a flash point of 230° F. PD-23 hydrocarbon is used in household products such as furniture polishes, household cleaners, liquid candles, and hand cleaners.

A gel was prepared from the ETPA made according to Example 3. The gel was made by heating 20% (by weight) of the ETPA in PD-23 until the ETPA had dissolved. The solution was allowed to cool and a clear, hard gel was formed.

EXAMPLE 14

ETPA Gel With KLEAROL Hydrocarbon

This example shows how the ETPA prepared as in Example 3 can be used to gel a low viscosity, white mineral oil. The mineral oil used was Klearol® (Witco Corp., Greenwich, Conn.) which has a viscosity of 7–10 cSt at 40° C. and a flash point of 310° F. Klearol® mineral oil is used in personal care products such as cleansing creams, hand cleansers, costume makeup, lipsticks, and hair care products. When gelled with the ETPA at 20% solids, the gel was clear and hard.

EXAMPLE 15

ETPA Gel With KAYDOL Hydrocarbon

This example shows how the ETPA prepared as in Example 3 can be used to gel a high viscosity, white mineral oil. The mineral oil used was Kaydol®, which has a viscosity of 64–70 cSt at 40° C., a flash point of 430° F. and is available from Witco Corp. Kaydol® mineral oil is used in bath oil, suntan oil, moisturizing creams, and foundation makeup. When gelled with the ETPA at 30% solids, the gel was clear and hard.

EXAMPLE 16

ETPA Gel With A Monofunctional Ester Solvent

This example shows how the ETPA prepared as in Example 3 can be used to gel a mono-functional ester. The ester was a $C_{12-15}$ alkyl benzoate called Finsolv® TN, made by Fintex (Elmwood Park, N.J.). When gelled with the ETPA at 10% solids, the gel was clear and hard.

EXAMPLE 17

ETPA Gel With A Monofunctional Ester Solvent

This example shows how the ETPA prepared as in Example 3 can be used to gel a mono-functional ester. The ester was isopropyl isostearate (Unimate IPIS, made by Union Camp, Wayne, N.J.). When gelled with the ETPA at 20% solids, the gel was clear and hard.

EXAMPLE 18

ETPA Gel With A Multifunctional Ester Solvent

This example shows that a multi-functional ester can be gelled with the ETPA prepared as in Example 3. The ester was castor oil. When combined with the ETPA at 20% solids, a clear, hard gel was formed.

EXAMPLE 19

ETPA Gel With Terpene Hydrocarbon Solvent

This example shows that a terpene hydrocarbon solvent can be gelled with an ETPA. An ETPA was prepared using the procedure of Example 8. The resultant ETPA was combined with limonene at 20% solids to yield a clear, firm gel.

EXAMPLE 20

Comparative Example

In this comparative example, an ETPA was made by first synthesizing a polyamide from Empol 1008 hydrogenated dimer (Henkel Corp. Ambler, Pa.) and EDA resulting in a polyamide with an amine number of 3 and a softening point of 115° C. 100 g of this polyamide was heated under nitrogen with 66 g of Empol 1008 at 230° C. for 50 minutes. The mixture was cooled to 110° C. and 30 g of ethanol and 2 ml of HCl were added. The mixture was heated under reflux conditions and the temperature was allowed to reach 230° C. The acid number was checked periodically and ethanol was added (at 110° C.) until the acid number was less than 30. At 230° C., vacuum was held on the mixture for 0.5 h and the ETPA was poured. The resultant ETPA has an acid number of 25 and a softening point of 80° C.

The ETPA was combined with tetradecane at 20% and heated until the ETPA dissolved. Upon cooling, an opaque, soft gel formed that showed syneresis.

EXAMPLE 21

Comparative Example

This comparative example repeats Example 20, however the esterification was done at much lower temperatures. The polyamide described in Example 20 (softening point=115° C.) was heated under reflux with Empol 1008 at 230° C. in the same proportions as in Example 20 for 50 min. This mixture was then cooled to 25° C. and ethanol and HCl were added in the same proportions as in Example 20. The mixture was heated under reflux at 80–85° C. for eight hours and the excess ethanol was removed in a nitrogen stream at 100° C. The resultant product had an acid number of 17 and a softening point of 83° C. This material at 20% level was then heated in tetradecane until dissolved. After the mixture cooled, an opaque, soft gel formed that showed syneresis.

EXAMPLE 22

Comparative Example

This comparative example shows that the ETPA made in Example 21 is capable of thickening linseed oil, a component of alkyd paints. The ETPA made in Example 21 at 10% level was heated in linseed oil until dissolved. Upon cooling, an opaque, thickened product was formed.

EXAMPLE 23

This example shows that the ETPA made according to the present method thickens linseed oil. The ETPA made in Example 3 at 10% level was heated in linseed oil until dissolved. Upon cooling, an opaque, thickened product was formed.

EXAMPLE 24

This example shows that an ETPA can be used to gel an oil-based mixture with an active ingredient. 10 g of the ETPA prepared as in Example 8 was heated in 15 g methyl salicylate, 4 g menthol (active ingredient), and 21 g of KAYDOL (white mineral oil) until the ETPA was dissolved. When the solution cooled, a clear, firm gel was formed.

EXAMPLE 25

Candle Preparation

This Example demonstrates that an ETPA resin can be used to make a clear candle. The candle was prepared by combining 60 parts DRAKEOL 7 mineral oil (from Penreco, a division of Pennzoil Products Company, Karns City, Pa.) and 40 parts of the ETPA prepared in Example 8, and heating the combination to about 110° C. until a clear, visually homogeneous solution is obtained. The hot mixture is then poured into a shallow dish that contains a wick. Upon cooling, a clear, freestanding candle is formed. The candle does not emit smoke when lit, and no discoloration was observed after burning.

Throughout the present specification, where resins or reaction mixtures are described as including or comprising specific components or materials, it is contemplated by the inventors that the resins or reaction mixtures of the present invention also consist essentially of, or consist of, the recited components or materials. Accordingly, throughout the present disclosure any described composition (resin or reaction mixture) of the present invention can consist essentially of, or consist of, the recited components or materials.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for preparing a resin composition comprising ester-terminated polyamide, the method comprising reacting x equivalents of carboxylic acid from diacid or a reactive equivalent thereof, y equivalents of amine from diamine and z equivalents of hydroxyl from monoalcohol or a reactive equivalent thereof, wherein at least about 50% of the carboxylic acid equivalents are from polymerized fatty acid, monoalcohol is substantially the only monofunctional reactant used to form the resin, the monoalcohol has at least four carbon atoms, $0.9 \leq \{x/(y+z)\} \leq 1.1$, and $0.1 \leq \{z/(y+z)\} \leq 0.7$.

2. The method of claim 1 wherein a reaction mixture comprising diacid, diamine and monoalcohol are reacted to yield the resin.

3. The method of claim 1 wherein a reaction mixture consisting essentially of x equivalents of carboxylic acid from diacid, y equivalents of amine from diamine and z equivalents of hydroxyl from monoalcohol is heated to yield the resin.

4. The method of claim 1 wherein all equivalents of carboxylic acid come from polymerized fatty acid.

5. The method of claim 1 wherein between 1% and 50% of the carboxylic acid equivalents come from a diacid of the formula HOOC—$R^2$—COOH wherein $R^2$ is a $C_{4-19}$ hydrocarbon group.

6. The method of claim 1 wherein the diamine has the formula $H_2N$—$R^3$—$NH_2$ and $R^3$ is a $C_{2-36}$ hydrocarbon group.

7. The method of claim 1 wherein at least 50% of the amine equivalents are contributed by a diamine of the formula $H_2N$—$R^3$—$NH_2$ wherein $R^3$ is a $C_{2-36}$ hydrocarbon group, and at least 1% of the amine equivalents are contributed by one or more diamines selected from

and $H_2N$—$R^3$—$NH_2$, wherein $R^3$ is selected from polyalkylene oxide, polyalkylene amine, or

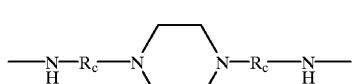

wherein $R_c$ is a $C_{1-3}$ alkyl group.

8. The method of claim 1 wherein the monoalcohol has the formula $R^1$—OH and $R^1$ is a $C_{12-22}$ hydrocarbon group.

9. The method of claim 1 wherein x/(y+z) is substantially equal to 1.

10. The method of claim 1 wherein 0.2≦{z/(y+z)}≦0.5.

11. The composition prepared by the method of claim 1.

12. The composition of claim 11 further comprising a low polarity liquid.

13. The composition of claim 12 which is transparent or translucent.

14. The composition of claim 12 which is a self-supporting gel.

15. The composition of claim 12 which does not display syneresis.

16. The composition of claim 12 having at least about 5 weight percent and less than about 50 weight percent of the resin composition, based on the total weight of low polarity liquid and the resin composition.

17. The composition of claim 12 wherein the low polarity liquid comprises a hydrocarbon.

18. The composition of claim 17 wherein the hydrocarbon is an oil.

19. A method for preparing a transparent or translucent gel, comprising combining a low polarity liquid with a resin composition, the resin composition comprising ester-terminated polyamide of formula (1):

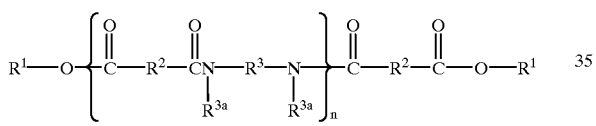

(1)

wherein n designates a number of repeating units such that ester groups are from 10% to 50% of the total of the ester and amide groups;

$R^1$ at each occurrence is independently selected from an alkyl or alkenyl group containing at least 4 carbon atoms;

$R^2$ at each occurrence is independently selected from a $C_{4\text{-}42}$ hydrocarbon group with the proviso that at least 50% of the $R^2$ groups have 30–42 carbon atoms;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1\text{-}10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen.

20. A method for preparing a transparent or translucent gel, comprising combining a low polarity liquid with a resin according to claim 11.

21. A cosmetic comprising a resin composition comprising ester-terminated polyamide of formula (1):

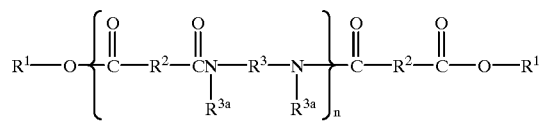

(1)

wherein n designates a number of repeating units such that ester groups are from 10% to 50% of the total of the ester and amide groups;

$R^1$ at each occurrence is independently selected from an alkyl or alkenyl group containing at least 4 carbon atoms;

$R^2$ at each occurrence is independently selected from a $C_{4\text{-}42}$ hydrocarbon group with the proviso that at least 50% of the $R^2$ groups have 30–42 carbon atoms;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1\text{-}10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen.

22. A cosmetic comprising the composition of claim 11.

23. A personal care product comprising a resin composition comprising ester-terminated polyamide of formula (1):

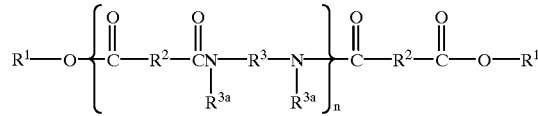

(1)

wherein n designates a number of repeating units such that ester groups are from 10% to 50% of the total of the ester and amide groups;

$R^1$ at each occurrence is independently selected from an alkyl or alkenyl group containing at least 4 carbon atoms;

$R^2$ at each occurrence is independently selected from a $C_{4\text{-}42}$ hydrocarbon group with the proviso that at least 50% of the $R^2$ groups have 30–42 carbon atoms;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1\text{-}10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen.

24. A personal care product comprising the composition of claim 11.

* * * * *